United States Patent
Tu et al.

(10) Patent No.: US 10,420,759 B2
(45) Date of Patent: Sep. 24, 2019

(54) SMALL MOLECULE THERAPIES FOR PULMONARY HYPERTENSION

(71) Applicant: Creighton University, Omaha, NE (US)

(72) Inventors: Yaping Tu, Omaha, NE (US); Yan Xie, Omaha, NE (US); Peter Abel, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 15/482,014

(22) Filed: Apr. 7, 2017

(65) Prior Publication Data

US 2017/0290819 A1    Oct. 12, 2017

Related U.S. Application Data

(60) Provisional application No. 62/319,827, filed on Apr. 8, 2016.

(51) Int. Cl.
| | | |
|---|---|---|
| *A61K 31/4545* | (2006.01) | |
| *A61K 45/06* | (2006.01) | |
| *A61K 31/4412* | (2006.01) | |
| *A61K 9/00* | (2006.01) | |
| *A61K 31/4418* | (2006.01) | |

(52) U.S. Cl.
CPC .......... *A61K 31/4545* (2013.01); *A61K 9/007* (2013.01); *A61K 31/4412* (2013.01); *A61K 31/4418* (2013.01); *A61K 45/06* (2013.01)

(58) Field of Classification Search
None
See application file for complete search history.

(56) References Cited

U.S. PATENT DOCUMENTS

2012/0192861 A1* 8/2012 Surber ................. A61K 9/0078
128/200.16

OTHER PUBLICATIONS

Zhen et al—STN Accession No. 2012:1713756 (Year: 2012).*
Zhen et al—Derwent Accession No. 2013-D15272 (Year: 2013).*
Lettieri et al (Chest 129:746-752, 2006—Abstract only) (Year: 2006).*
Farkas et al (Am J Respir Cell Mol Biol 45:1-15, 2011) (Year: 2011).*

Bockman et al., "Alpha-2 adrenoceptor subtype causing nitric oxide-mediated vascular relaxation in rats," J. Pharmacol. Exp. Ther., Sep. 1996, 278:1235-1243.
Fagan et al., "The pulmonary circulation of homozygous or heterozygous eNOS-null mice is hyperresponsive to mild hypoxia," J. Clin. Invest., Jan. 1999, 103:291-299.
Galiè et al., "2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT)," Eur. Heart J., 2015, 37: 67-119.
Jiang et al., "Phosphoinositide 3-Kinase γ Regulates Airway Smooth Muscle Contraction by Modulating Calcium Oscillations," J. Pharmacol. Exp. Ther., 2010, 334:703-709.
Ma et al., "Synthesis and biological evaluation of the pirfenidone derivatives as antifibrotic agents," Bioorganic & Medicinal Chemistry Letters, Jan. 2014, 24: 220-223.
Ma et al., "Synthesis of Pirfenidone," Chinese J. Pharm, 2006, 37: 372-373 (with English abstract).
McLaughlin et al, "ACCF/AHA 2009 expert consensus document on pulmonary hypertension: a report of the American College of Cardiology Foundation Task Force on Expert Consensus Documents and the American Heart Association: developed in collaboration with the American College of Chest Physicians, American Thoracic Society, Inc., and the Pulmonary Hypertension Association," Circulation, Apr. 2009, 119: 2250-94.
Morrell et al., "Cellular and Molecular Basis of Pulmonary Arterial Hypertension," J Am Coll Cardiol., 2009, 54: S20-31.
Perez-Joghbi and Sanderson, "Endothelin-induced contraction of bronchiole and pulmonary arteriole smooth muscle cells is regulated by intracellular Ca2+ oscillations and Ca2+ sensitization," Am. J. Physiol., 2007, 293:L1000-L1011.
Sakao et al., "Endothelial cells and pulmonary arterial hypertension: apoptosis, proliferation, interaction and transdifferentiation," Respir Res., 2009, 10:95.
Schweer, "Die Synthese Von 1-(P-Hydroxy-Phenyl)-2-Amino-Athanol-1-(1-14c)-Hydrochlorid," Atompraxis, 1966, 12: 85-86 (with English translation).
Simonneau et al., "Updated Clinical Classification of Pulmonary Hypertension," J Am Coll Cardiol., Jun. 2009, 54: S43-54.
Stamler et al., "Nitric Oxide Regulates Basal Systemic and Pulmonary Vascular Resistance in Healthy Humans," May 1994, Circulation, 89: 2035-2040.
Steudel et al., "Pulmonary Vasoconstriction and Hypertension in Mice With Targeted Disruption of the Endothelial Nitric Oxide Synthase (NOS 3) Gene," Jul. 1997, Circ. Res., 81:34-41.

* cited by examiner

*Primary Examiner* — Craig D Ricci
(74) *Attorney, Agent, or Firm* — Fish & Richardson P.C.

(57) ABSTRACT

The present disclosure relates to pirfenidone (5-methyl-1-phenyl-2-(1H)-pyridone) and its derivatives and pharmaceutically acceptable salts thereof, use of these compounds as a medicament, and for the manufacture of a medicament for treating or delaying the onset or development of pulmonary hypertension.

14 Claims, 6 Drawing Sheets

Intact isolated pulmoanry artery rings

SMALL MOLECULE THERAPIES FOR PULMONARY HYPERTENSION

CROSS-REFERENCE TO RELATED APPLICATIONS

This application claims the benefit of U.S. Provisional Application Ser. No. 62/319,827, filed Apr. 8, 2016, the disclosure of which is incorporated herein by reference in its entirety.

TECHNICAL FIELD

The present application describes compounds (e.g., pirfenidone and derivatives thereof) which are useful in methods of treating or delaying the onset or development of pulmonary hypertension (e.g., pulmonary arterial hypertension). Also provided are methods of reducing mean pulmonary arterial pressure and methods of activating endothelial nitric oxide synthase enzyme.

BACKGROUND

Pulmonary hypertension (PH) is a generic term for a group of conditions characterized by elevated blood pressure in the arteries of the lungs (pulmonary arteries). In patients with PH, characteristic changes occur within the pulmonary circulation. These changes include thickening of the linings and obstruction of the small pulmonary blood vessels. As a result of these changes, pressure in the pulmonary circulation rises, and resistance in the blood flowing through the vessels increases. This increased resistance puts a strain on the right side of the heart as it must work harder to pump blood to the lungs. This strain can cause the heart to enlarge, leading to eventual heart failure.

PH is defined as persistently elevated mean pulmonary arterial pressure (MPAP)≥25 mmHg at rest. The definitive diagnosis of PH is made by right heart catheterization (see, e.g., Galiè N. et al., Eur. Heart J. 2015, 29) to measure pressure in the pulmonary circulation which is elevated due to sustained vasoconstriction and vascular remodeling. Vasoconstrictors such as serotonin (5-HT), endothelin-1 (ET-1), and thromboxane, activate signaling cascades in the vascular smooth muscle that cause the sustained vasoconstriction. The World Health Organization (WHO) classification of PH includes five groups (McLaughlin V V, et al, Circulation, 2009, 119: 2250-94; Simonneau G, et al, J Am Coll Cardiol. 2009, 54: S43-54). Pulmonary arterial hypertension (PAH) is WHO group 1. PAH is a particularly severe form of PH characterized by narrowing and obstruction of the precapillary pulmonary arteries leading to increased pulmonary vascular resistance, right-sided heart failure, and premature death. PAH mainly affects young and middle-aged women. The other four types of PH are venous, hypoxic, thromboembolic, and miscellaneous PH.

SUMMARY

Current methods of treating PH focus on prolonging patient lifespan and enhancing patient quality of life. Such methods include administration of: vasodilators such as prostacyclin, epoprostenol, and sildenafil; endothelin receptor antagonists; calcium channel blockers; anticoagulants; supplemental oxygen therapy; and diuretics. When medical treatment fails, the final therapeutic option is lung and/or heart-lung transplantation. Each of these methods, however, suffers from one or multiple drawbacks such as lack of effectiveness, serious side effects, low patient compliance, or high cost. Accordingly, new pulmonary antihypertensive medications are needed.

The present application discloses that 5-methyl-1-phenyl-2-(1H)-pyridone (pirfenidone) and its derivatives CXN-8, CXN-9, and CXN-16 offer a new therapeutic tool to treat PH as a potent vasodilator via both NO-dependent and NO-independent signaling pathways.

The present application provides, inter alia, a method of treating pulmonary hypertension in a subject, comprising administering to the subject a therapeutically effective amount of a compound of Formula (V):

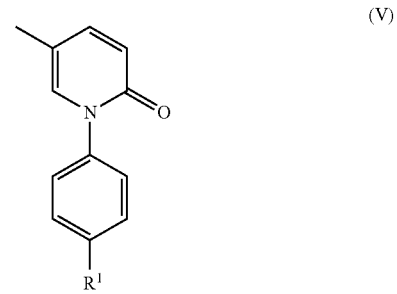

(V)

or a pharmaceutically acceptable salt thereof, wherein:
$R^1$ is selected from the group consisting of H and —($C_{1-6}$ alkoxy)-($NR^2R^3$); and
$R^2$ and $R^3$ are each an independently selected $C_{1-6}$ alkyl group; or
$R^2$ and $R^3$, together with the nitrogen atom to which they are attached, form a monocyclic 4-6 membered heterocycloalkyl ring.

In some embodiments, the pulmonary hypertension comprises one or more of pulmonary arterial hypertension, pulmonary venous hypertension, hypoxic pulmonary hypertension, thromboembolic pulmonary hypertension, and miscellaneous pulmonary hypertension. In some embodiments, the pulmonary hypertension comprises pulmonary arterial hypertension.

The present application further provides a method of reducing mean pulmonary arterial pressure in a subject, comprising administering to the subject a therapeutically effective amount of a compound of Formula (V):

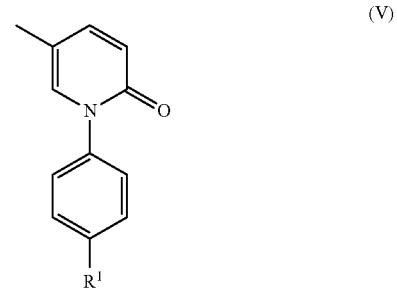

(V)

or a pharmaceutically acceptable salt thereof, wherein:
$R^1$ is selected from the group consisting of H and —($C_{1-6}$ alkoxy)-($NR^2R^3$); and
$R^2$ and $R^3$ are each an independently selected $C_{1-6}$ alkyl group; or
$R^2$ and $R^3$, together with the nitrogen atom to which they are attached, form a monocyclic 4-6 membered heterocycloalkyl ring.

The present application further provides a method of activating endothelial nitric oxide synthase enzyme in a subject, comprising administering to the subject a therapeutically effect amount of a compound of Formula (V):

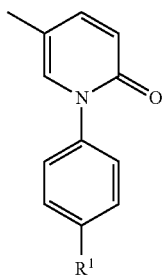

(V)

or a pharmaceutically acceptable salt thereof, wherein:

$R^1$ is selected from the group consisting of H and —($C_{1-6}$ alkoxy)-($NR^2R^3$); and $R^2$ and $R^3$ are each an independently selected $C_{1-6}$ alkyl group; or $R^2$ and $R^3$, together with the nitrogen atom to which they are attached, form a monocyclic 4-6 membered heterocycloalkyl ring.

In some embodiments, the methods provided herein further comprise administering to the subject a therapeutically effective amount of a compound selected from the group consisting of a vasodilator, an endothelin receptor antagonist, a calcium channel blocker, an anticoagulant, a diuretic, an anti-bacterial agent, an anti-microbial agent, or an anesthetic. In some embodiments, the vasodilator is selected from the group consisting of nitric oxide, acetylcholine, prostacyclin, epoprostenol, and sildenafil. In some embodiments, the methods provided herein further comprise administering to the subject supplemental oxygen therapy.

In some embodiments, the therapeutically effective amount of a compound of Formula (V) or a pharmaceutically acceptable salt thereof, is about 70% or less than the amount that causes an undesirable side effect in the subject. In some embodiments, the therapeutically effective amount is about 50% or less than the amount that causes an undesirable side effect in the subject. In some embodiments, the undesirable side effect comprises one or more of drowsiness, gastrointestinal distress, and photosensitivity rash.

In some embodiments, the administration is oral administration. In some embodiments, the administration is pulmonary administration.

The present application further provides a method of activating endothelial nitric oxide synthase enzyme in a cell or tissue, comprising contacting the cell or tissue with a compound of Formula (V):

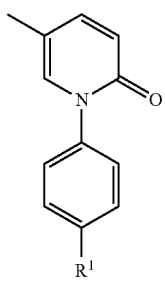

(V)

or a pharmaceutically acceptable salt thereof, wherein:

$R^1$ is selected from the group consisting of H and —($C_{1-6}$ alkoxy)-($NR^2R^3$); and $R^2$ and $R^3$ are each an independently selected $C_{1-6}$ alkyl group; or $R^2$ and $R^3$, together with the nitrogen atom to which they are attached, form a monocyclic 4-6 membered heterocycloalkyl ring.

In some embodiments of a compound of Formula (V), or a pharmaceutically acceptable salt thereof, $R^1$ is H.

In some embodiments of a compound of Formula (V), or a pharmaceutically acceptable salt thereof, $R^2$ and $R^3$ are each an independently selected $C_{1-3}$ alkyl. In some embodiments, $R^1$ is —$OCH_2CH_2CH_2CH_2N(CH_3)_2$.

In some embodiments of a compound of Formula (V), or a pharmaceutically acceptable salt thereof, $R^1$ is —($C_{1-6}$ alkoxy)-(4-6 membered heterocycloalkyl). In some embodiments, $R^1$ is —$OCH_2CH_2CH_2$-(4-6 membered heterocycloalkyl) or —$OCH_2CH_2CH_2CH_2$-(4-6 membered heterocycloalkyl).

In some embodiments of a compound of Formula (V), or a pharmaceutically acceptable salt thereof, $R^1$ is selected from the group consisting of

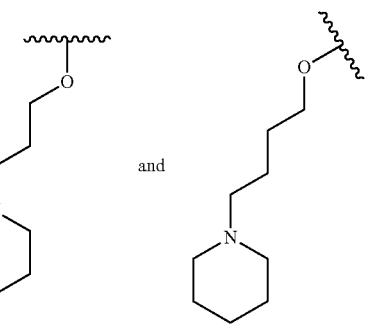

and

In some embodiments, the compound of Formula (V) is selected from the group consisting of:

5-methyl-1-phenylpyridin-2(1H)-one;

5-methyl-1-(4-(3-(piperidin-1-yl)propoxy)phenyl)pyridin-2(1H)-one;

5-methyl-1-(4-(4-(piperidin-1-yl)butoxy)phenyl)pyridin-2(1H)-one; and 1-(4-(4-(dimethylamino)butoxy)phenyl)-5-methylpyridin-2(1H)-one;

or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 1A shows a concentration-response curve of 5-HT-induced constriction of mouse pulmonary arteries. Reduction in artery lumen area was fitted with a logistic function curve. FIG. 1B shows concentration-response curves of pirfenidone and CXN-8, CXN-9, and CXN-16 induced relaxation of mouse pulmonary arteries pre-constricted with 100 nM 5-HT. Data are expressed as % relaxation of the pre-constriction to 5-HT. Points are mean±S.E. (n=6 from 3-5 mice).

FIG. 2A shows a concentration-response curve of 5-HT-induced constriction of mouse pulmonary arteries. The 5-HT-induced contraction is expressed as a percentage of KCl (60 mM)-induced constriction (mean±S.E., n=3). FIGS. 2B-2D show concentration-response curves of pirfenidone and CXN-8-induced relaxation of intact extralobar pulmonary arteries pre-constricted with 250 nM 5-HT (FIG. 2B), 20 nM thromboxane A2 receptor agonist U46619 (FIG. 2C), and 10 nM ET-1 (FIG. 2D). Data are expressed as % relaxation of the pre-constriction to vasoconstrictors 5-HT, U46619, or ET-1 (mean±S.E., n=7).

FIG. 5A shows right ventricular systolic pressure (RVSP) in wild type (WT) and eNOS KO (eNOS−/−) mice. Values are means±S.E., wild type (n=3) and eNOS−/− mice (n=3), *p<0.01 vs. WT mice. Representative traces (FIG. 5B) and summarized data (FIG. 5C) showing that CXN-8 reduced RVSP of eNOS−/− mice. RVSP of eNOS−/− mice was measured at baseline and in response to different doses of CXN-8 injected via the femoral vein. Data are presented as mean±S.E. (n=3), *p<0.01 vs. baseline.

FIG. 6A shows RVSP in wild type (WT) and RGS2 KO (RGS2−/−) mice. Values are means±S.E., wild type (n=3) and RGS2−/− mice (n=8), *p<0.001 vs. WT mice. FIG. 6B shows Fulton Index of WT and RGS2 KO mice. Right ventricular (RV) hypertrophy measured as the RV weight over left ventricular (LV) plus interventricular septum (S) weight ratio (RV/[LV+S])=Fulton index. Values are mean±S.E., WT (n=3) and RGS2 KO mice (n=8), *p<0.001 vs. WT mice. FIG. 6C shows representative traces (top) and summarized data (bottom) showing that CXN-8 reduces RVSP in RGS2 KO mice. RVSP of RGS2 KO mice was measured at baseline and in response to different doses of CXN-8 injected via the femoral vein. Data are presented as mean±S.E. (n=8), *p<0.01 vs. baseline (bottom).

FIG. 7A shows RVSP in normoxic and hypoxic mice. Values are means±S.E., normoxic (n=7) and hypoxic mice (n=8), *p<0.001 vs. normoxic mice. FIG. 7B shows Fulton Index of normoxic and hypoxic mice. Right ventricular (RV) hypertrophy measured as the RV weight over left ventricular (LV) plus interventricular septum (S) weight ratio (RV/[LV+S])=Fulton index. Values are mean±S.E., normoxic (n=7) and hypoxic mice (n=8), *p<0.001 vs. normoxic mice. FIG. 7C shows that CXN-8 reduces RVSP in hypoxic mice. RVSP of hypoxic mice was measured at baseline and in response to different doses of CXN-8 injected via the femoral vein. Data are presented as mean±S.E. (n=3), *p<0.01 vs. baseline.

DETAILED DESCRIPTION

Compounds and Synthesis

Figures 1A, 1B:
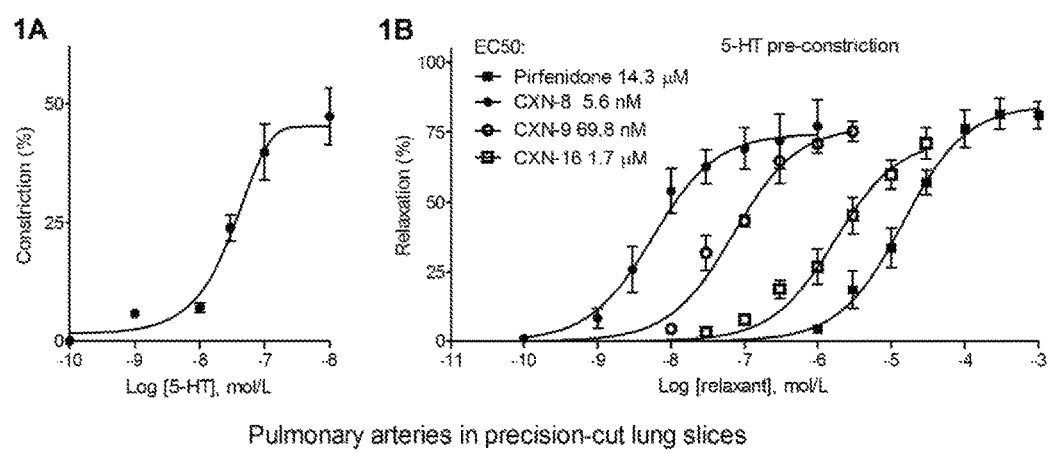
FIGS. 1A-1B show that pirfenidone and its derivatives, CXN-8, CXN-9, and CXN-16, induced relaxation of pre-constricted pulmonary arteries in mouse precision-cut lung slices.

The present application provides compounds of Formula (V):

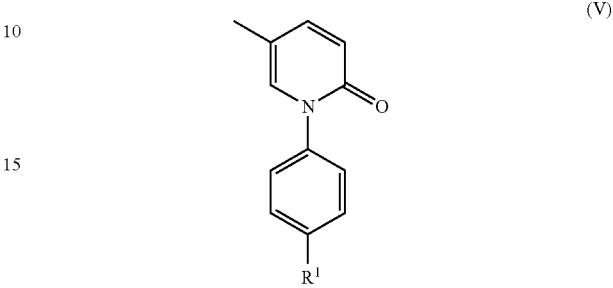

or a pharmaceutically acceptable salt thereof, wherein:

$R^1$ is selected from the group consisting of H and —($C_{1-6}$ alkoxy)-($NR^2R^3$); and $R^2$ and $R^3$ are each an independently selected $C_{1-6}$ alkyl group; or $R^2$ and $R^3$, together with the nitrogen atom to which they are attached, form a monocyclic 4-6 membered heterocycloalkyl ring.

In some embodiments, $R^1$ is H.

In some embodiments, $R^2$ and $R^3$ are each an independently selected $C_{1-3}$ alkyl group. In some embodiments, $R^2$ and $R^3$ are the same. In some embodiments, $R^2$ and $R^3$ are different. In some embodiments, $R^2$ and $R^3$ are each methyl. In some embodiments, $R^1$ is —($C_{1-6}$ alkoxy)-N($CH_3$)$_2$. In some embodiments, $R^1$ is —$OCH_2CH_2CH_2CH_2$—($NR^2R^3$). In some embodiments, $R^1$ is —$OCH_2CH_2CH_2CH_2N(CH_3)_2$.

In some embodiments, $R^2$ and $R^3$, together with the nitrogen atom to which they are attached, form a monocyclic 4-6 membered heterocycloalkyl ring. In some embodiments, $R^1$ is —($C_{1-6}$ alkoxy)-(4-6 membered heterocycloalkyl). In some embodiments, $R^1$ is —($C_{1-6}$ alkoxy)-(piperidinyl). In some embodiments, $R^1$ is —$OCH_2CH_2CH_2$-(4-6 membered heterocycloalkyl). In some embodiments, $R^1$ is —$OCH_2CH_2CH_2CH_2$-(4-6 membered heterocycloalkyl). In some embodiments, $R^1$ is selected from the group consisting of

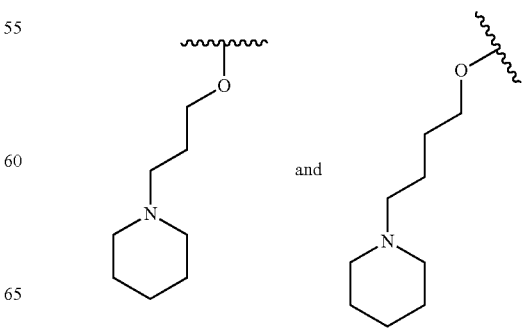

and

In some embodiments, the compound is selected from the group consisting of:

5-methyl-1-phenylpyridin-2(1H)-one (i.e., pirfenidone);
5-methyl-1-(4-(3-(piperidin-1-yl)propoxy)phenyl)pyridin-2(1H)-one (i.e., CXN-8);
5-methyl-1-(4-(4-(piperidin-1-yl)butoxy)phenyl)pyridin-2(1H)-one (i.e., CXN-9);
and
1-(4-(4-(dimethylamino)butoxy)phenyl)-5-methylpyridin-2(1H)-one (i.e., CXN-16);
or a pharmaceutically acceptable salt thereof.

Pirfenidone (i.e., 5-methyl-1-phenyl-2-(1H)-pyridone or 5-methyl-1-phenylpyridin-2(1H)-one) is a drug developed by several companies worldwide for the treatment of idiopathic pulmonary fibrosis (IPF). In 2011, pirfenidone was approved for use in Europe for IPF under the trade name ESBRIET®, and was approved in the United States in October 2014 under the same name. The structure of pirfenidone is shown in Formula (I) and its derivative CXN-8 has the structure of Formula (II), CXN-9 has the structure of Formula (III), and CXN-16 has the structure of Formula (IV).

Formula (II)

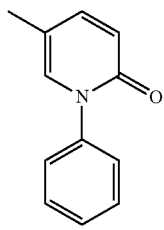

CXN-8

Formula (II)

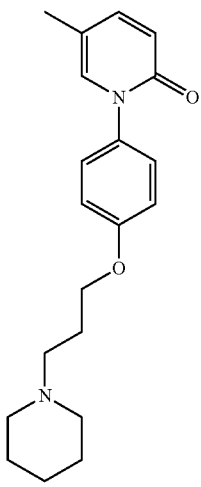

CXN-8

Formula (III)

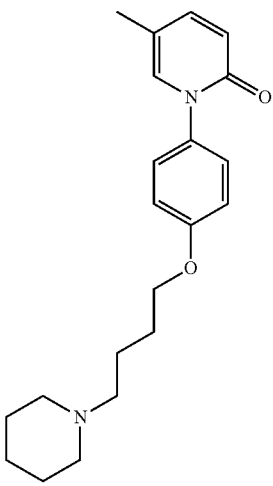

CXN-9

Formula (IV)

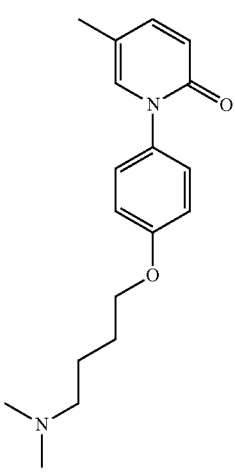

CXN-16

The compounds of Formulas (II)-(IV) can be synthesized, for example, using methods described by Ma et al (*Bioorganic & Medicinal Chemistry Letters,* 2014, 24: 220-223), as shown in Scheme 1. The starting reagents were chosen to provide the desired substitutions in the final product. These reagents can themselves be prepared using known methods. For example, starting material 1 was prepared as previously reported (Ma, Z. et al *J. Pharm.* 2006, 37, 372). Intermediate 2 was generated by protection of 4-bromophenol with benzyl bromide (see e.g., Schweer, K. H. S. *Atompraxis,* 1966, 12, 85). Using cuprous iodide as a catalyst, 3 was synthesized by the Ullmman coupling reaction of 1 with 2 in dry DMF (Scheme 1, Step a). Intermediate 4 was obtained by benzyl deprotection of 3 in THF with 5% Pd/C under $H_2$ atmosphere (Scheme 1, Step b). After the reaction between intermediate 4 and alkyl dihalide at reflux temperature, compound 5 was achieved (Scheme 1, Step c). Finally, CXN-8, CXN-9, or CXN-16 was obtained by amination reaction of 5 with an appropriate amine (Scheme 1, step d).

Scheme 1.

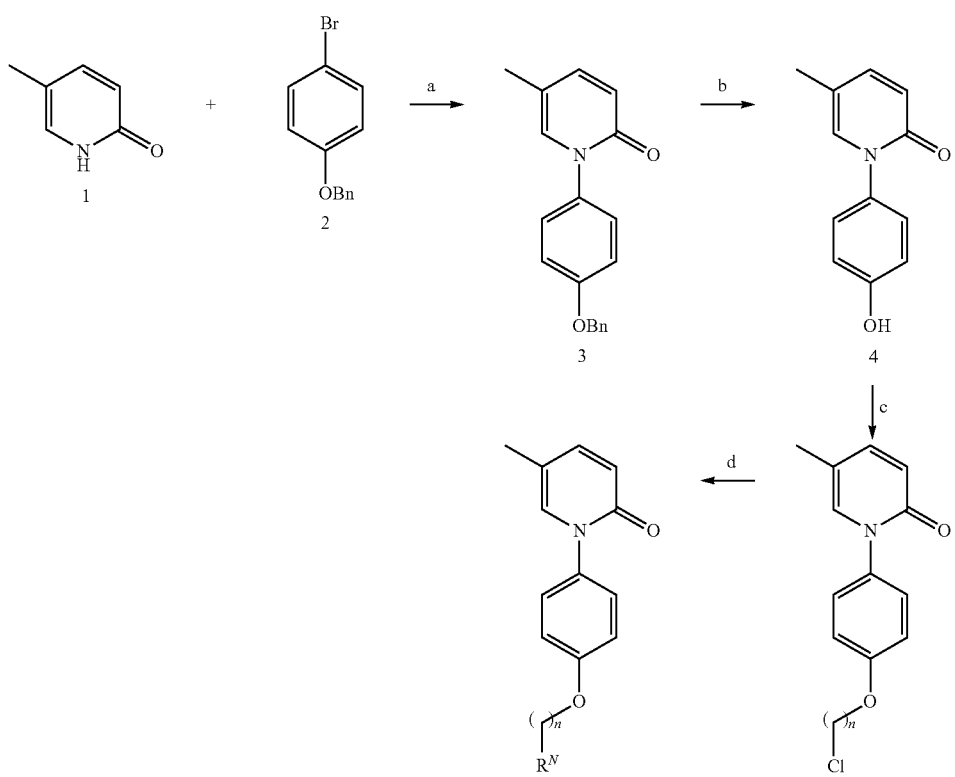

$R^N$ = piperidinyl or dimethylamino
n = 3 or 4

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$—includes both —NR(CR'R")$_n$— and —(CR'R")$_n$NR—. Where the structure clearly requires a linking group, the Markush variables listed for that group are understood to be linking groups.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, and 6-membered heterocycloalkyl groups. Exemplary heterocycloalkyl groups include, but are not limited to, oxetanyl, azetidinyl, morpholinyl, thiomorpholinyl, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo (=O). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 double bonds. In some embodiments, the heterocycloalkyl has 4-6 ring atoms with 1 or 2 heteroatoms independently selected from nitrogen, oxygen, and sulfur. In some embodiments, the heterocycloalkyl has 4-6 ring atoms with 1 or 2 heteroatoms which are nitrogen.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Methods of Use

The present application further provides a method of treating pulmonary hypertension (PH) in subject. As used herein the term "pulmonary hypertension" is defined as an increase in mean pulmonary arterial pressure (MPAP)≥25 mmHg at rest. In some embodiments, the PH is diagnosed using right heart catheterization (see e.g., Galiè N. et al., *Eur. Heart J.* 2015, 29). In some embodiments, the methods of treating PH provided herein comprise administering to the subject a therapeutically effective amount of a compound of Formula (V):

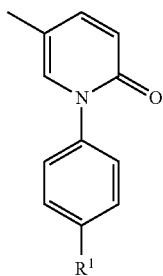

(V)

or a pharmaceutically acceptable salt thereof, wherein variable $R^1$ is defined according to the definition provided herein for compounds of Formula (V).

In some embodiments, the pulmonary hypertension (PH) comprises one or more of pulmonary arterial hypertension, pulmonary venous hypertension, hypoxic pulmonary hypertension, thromboembolic pulmonary hypertension, and miscellaneous pulmonary hypertension. In some embodiments, the pulmonary hypertension comprises pulmonary arterial hypertension. In some embodiments, the pulmonary hypertension comprises hypoxic pulmonary hypertension.

The present application further provides a method of reducing mean pulmonary arterial pressure (MPAP) in a subject, comprising administering to the subject a therapeutically effective amount of a compound of Formula (V):

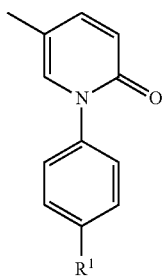

(V)

or a pharmaceutically acceptable salt thereof, wherein variable R' is defined according to the definition provided herein for compounds of Formula (V). In some embodiments, the MPAP is measured by right heart catheterization.

The present application further provides a method of activating endothelial nitric oxide synthase enzyme in a subject, comprising administering to the subject a therapeutically effect amount of a compound of Formula (V):

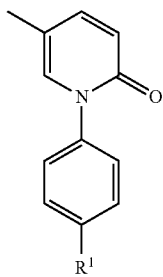

(V)

or a pharmaceutically acceptable salt thereof, wherein variable $R^1$ is defined according to the definition provided herein for compounds of Formula (V).

In some embodiments, administration of the compounds provided herein (e.g., a compound of any of Formulas (I)-(V)) improves vasorelaxation of the pulmonary arteries in the subject. In some embodiments, the vasorelaxation is improved by about 10% to about 99.9%, for example, about 10% to about 99.9%, about 10% to about 95%, about 10% to about 90%, about 10% to about 80%, about 10% to about 70%, about 10% to about 60%, about 10% to about 50%, about 10% to about 40%, about 10% to about 30%, about 10% to about 20%, about 20% to about 99.9%, about 20% to about 95%, about 20% to about 90%, about 20% to about 80%, about 20% to about 70%, about 20% to about 60%, about 20% to about 50%, about 20% to about 40%, about 20% to about 30%, about 30% to about 99.9%, about 30% to about 95%, about 30% to about 90%, about 30% to about 80%, about 30% to about 70%, about 30% to about 60%, about 30% to about 50%, about 30% to about 40%, about 40% to about 99.9%, about 40% to about 95%, about 40% to about 90%, about 40% to about 80%, about 40% to about 70%, about 40% to about 60%, about 40% to about 50%, about 50% to about 99.9%, about 50% to about 95%, about 50% to about 90%, about 50% to about 80%, about 50% to about 70%, about 50% to about 60%, about 60% to about 99.9%, about 60% to about 95%, about 60% to about 90%, about 60% to about 80%, about 60% to about 70%, about 70% to about 99.9%, about 70% to about 95%, about 70% to about 90%, about 70% to about 80%, about 80% to about 99.9%, about 80% to about 95%, about 80% to about 90%, about 90% to about 99.9%, about 90% to about 95%, or about 95% to about 99.9%, compared to the pulmonary arteries prior to administering the compound or salt provided herein.

The present application further provides a method of activating endothelial nitric oxide synthase enzyme in a cell or tissue (e.g., in vitro or in vivo), comprising contacting the cell or tissue with a compound of Formula (V):

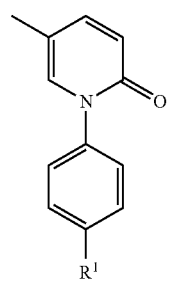

(V)

or a pharmaceutically acceptable salt thereof, wherein variable $R^1$ is defined according to the definition provided herein for compounds of Formula (V).

The present application further provides a method for treating a subject suffering from PH or a disease or condition that is a risk for developing PH. In some embodiments, the present application provides a method of preventing PH or preventing the development of PH in a subject, wherein the PH has an unknown cause; is inherited; is caused by drugs or toxins; is caused by conditions including, but not limited to, connective tissue disease, HIV infection, liver disease, congenital heart disease, sickle cell disease, or schistosomiasis; is caused by conditions that affect the arteries or veins and small blood vessels of the lungs; or any combination thereof. In some embodiments, the disease or condition at risk for developing PH is selected from the group consisting of lung disease and/or hypoxia such as chronic obstructive pulmonary disease, interstitial lung disease, pulmonary diseases with mixed restrictive and obstructive pattern, sleep-disordered breathing, alveolar hypoventilation disorders, chronic exposure to high altitude, and developmental abnormalities. In some embodiments, the method comprises administering to the subject a therapeutically or prophylactically effective amount (e.g., an amount effective to prevent the development of PH) of a compound provided herein (e.g., a compound of any of Formulas (I)-(V)), or a pharmaceutically acceptable salt thereof.

In some embodiments, the compound of Formula (V) is selected from the group consisting of:
5-methyl-1-phenylpyridin-2(1H)-one (i.e., pirfenidone);
5-methyl-1-(4-(3-(piperidin-1-yl)propoxy)phenyl)pyridin-2 (1H)-one (i.e., CXN-8);
5-methyl-1-(4-(4-(piperidin-1-yl)butoxy)phenyl)pyridin-2 (1H)-one (i.e., CXN-9); and
1-(4-(4-(dimethylamino)butoxy)phenyl)-5-methylpyridin-2 (1H)-one (i.e., CXN-16);
or a pharmaceutically acceptable salt thereof. In some embodiments, the compound of Formula (V) is 5-methyl-1-(4-(3-(piperidin-1-yl)propoxy)phenyl)pyridin-2(1H)-one (i.e., CXN-8), or a pharmaceutically acceptable salt thereof.

In some embodiments, the method comprises administering to the patient a therapeutically effective amount of a compound of Formula (V), or a pharmaceutically acceptable salt thereof, via oral or inhalation (i.e., pulmonary) administration. In some embodiments, the administration is oral administration. In some embodiments, the administration is inhalation (i.e. pulmonary) administration. In some embodiments, the method comprises administering to said patient a therapeutically effective amount of CXN-8 having a chemical structure of Formula (II) or a pharmaceutically acceptable salt thereof, via oral or inhalation (i.e., pulmonary) administration.

As used herein, the terms "subject" or "patient" refer to any animal, including mammals. Example subjects and patients include, but are not limited to, mice, rats, rabbits, dogs, cats, swine, cattle, sheep, horses, primates, and humans. In some embodiments, the subject or patient is a human.

The compounds, salts, and pharmaceutical compositions provided herein can be effective over a wide dosage range and are generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

In some embodiments, the therapeutically effective amount is an amount which will reduce MPAP in the subject to <25 mmHg. In some embodiments, the therapeutically effective amount is preferably about 70% or less (e.g., less than about 50%), of the amount that causes an undesirable side effect in the subject, such as, but not limited to, drowsiness, gastrointestinal distress, and photosensitivity rash. For example, in some embodiments the therapeutically effective amount administered to the subject is about 70% or less, about 60% or less, about 50% or less, about 40% or less, about 30% or less, about 20% or less, or about 10% or less of the amount that causes an undesirable side effect in the subject.

In various forms of these embodiments, the therapeutically effective dose is administered once daily. In various forms of these embodiments, the therapeutically effective dose is administered on consecutive days for at least a week, at least a month, at least a year, or on an as needed basis for the rest of the patient's life.

For the compounds and salts provided herein, the therapeutically or prophylactically effective amount can be estimated initially either in cell culture assays, e.g., of smooth muscle cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Compounds, salts, and pharmaceutical compositions that exhibit large therapeutic indices (>25) are preferred. However, compounds, salts, and pharmaceutical compositions that exhibit narrow therapeutic indices (<25) are also within the scope of the invention. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

In some embodiments, the methods provided herein further comprise administering to a subject a compound provided herein (e.g., a compound of Formula (V)), or a pharmaceutically acceptable salt thereof, in combination with one or more additional therapeutic agents such as, for example, vasodilators, endothelin receptor antagonists, calcium channel blockers, anticoagulants, diuretics, anti-bacterial agents, anti-microbial agents, or anesthetics (e.g., for use in combination with a surgical procedure). In some embodiments, the compounds and salts provided herein may be administered in combination with supplemental oxygen therapy.

Exemplary vasodilators include, but are not limited to, nitric oxide, acetylcholine, prostacyclin, epoprostenol, sildenafil, hydralazine, minoxidil, doxazosin, prazosin, and clonidine. In some embodiments, the vasodilator is selected from the group consisting of nitric oxide, acetylcholine, prostacyclin, epoprostenol, and sildenafil. In some embodiments, the vasodilator is selected from the group consisting of nitric oxide and acetylcholine.

Exemplary endothelin receptor antagonists include, but are not limited to, sitaxentan, ambrisentan, atrasentan, BQ-123, zibotentan, bosentan, macitentan, and tezosentan.

Exemplary calcium channel blockers include, but are not limited to, mibefradil, amlodipine, diltiazem, felodipine, isradipine, nicardipine, nifedipine, nisoldipine, and verapamil.

Exemplary anticoagulants include, but are not limited to, warfarin, dabigatran, apixaban, rivaroxaban, dalteparin, danaparoid, enoxaparin, fondaparinux, and lepirudin.

Exemplary diuretics include, but are not limited to, chlorothiazide, chlorthalidone, indapamide, hydrochlorothiazide, methyclothiazide, metolazone, bumetanide, furosemide, ethacrynic acid, torsemide, amiloride, spironolactone, and triamterene.

Exemplary anti-bacterial agents and/or anti-microbial agents include, but are not limited to, penicillins (e.g., penicillin, amoxicillin), cephalosporins (e.g., cephalexin), macrolides (e.g., erythromycin, clarithromycin, azithromycin), fluoroquinolones (ciprofloxacin, levofloxacin, ofloxacin) sulfonamides (e.g., trimethoprim, co-trimoxazole (trimethoprim/sulfamethoxazole), tetracyclines (e.g., tetracycline, doxycycline), and aminoglycosides (e.g., gentamicin, neomycin, and streptomycin).

Exemplary anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, and pentazocine).

In some embodiments, the additional therapeutic agent and/or supplemental oxygen therapy is administered simultaneously with a compound or salt provided herein. In some embodiments, the additional therapeutic agent and/or supplemental oxygen therapy is administered after administration of the compound or salt provided herein. In some embodiments, the additional therapeutic agent and/or supplemental oxygen therapy is administered prior to administration of the compound or salt provided herein. In some embodiments, the compound or salt provided herein is administered during a surgical procedure. In some embodiments, the compound or salt provided herein is administered in combination with an additional therapeutic agent and/or supplemental oxygen therapy during a surgical procedure.

Pharmaceutical Compositions and Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. In some embodiments, the pharmaceutical compositions contain, as the active ingredient, a compound provided herein, or a pharmaceutically acceptable salt thereof, in combination with one or more pharmaceutically acceptable carriers (e.g., excipients).

In some embodiments, the pharmaceutical compositions may be formulated with pharmaceutically acceptable excipients such as carriers, solvents, stabilizers, adjuvants, diluents, etc., depending upon the particular mode of administration and dosage form. In preparing the compositions provided herein, the active ingredient is typically mixed with an excipient, diluted by an excipient or enclosed within such a carrier in the form of, for example, a capsule or other container. When the excipient serves as a diluent, it can be a solid, semi-solid, or liquid material, which acts as a vehicle, carrier or medium for the active ingredient. Thus, the compositions can be in the form of tablets, pills, powders, lozenges, elixirs, ointments, suspensions, emulsions, solutions, syrups, aerosols (as a solid or in a liquid medium), soft and hard gelatin capsules, and sterile packaged powders.

Exemplary excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

Administration may be pulmonary (e.g., by inhalation or insufflation of powders or aerosols, including by nebulizer; intratracheal or intranasal) or oral. Conventional pharmaceutical carriers, aqueous, powder or oily bases, thickeners and the like may be necessary or desirable.

Formulations, e.g., for oral administration, are most typically solids, liquid solutions, emulsions, or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration.

In some embodiments, the methods provided herein comprise oral administration of a pharmaceutical composition comprising a compound of Formula (V), or a pharmaceutically acceptable salt thereof. In some embodiments, the methods provided herein comprise inhalation (i.e., pulmonary) administration of a pharmaceutical composition comprising a compound of Formula (V), or a pharmaceutically acceptable salt thereof.

The pharmaceutical compositions should generally be formulated to achieve a physiologically compatible pH, and may range from a pH of about 3 to a pH of about 11, preferably about pH 3 to about pH 7, depending on the formulation and route of administration. In some embodiments, it may be preferred that the pH is adjusted to a range from about pH 5.0 to about pH 8. Optionally, the pharmaceutical compositions may comprise a combination of the compounds described herein, or may include a second active ingredient (i.e., an additional therapeutic agent) provided herein. In some embodiments, the additional therapeutic agent is useful in the treatment or prevention of bacterial infection (e.g., anti-bacterial or anti-microbial agents).

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Pirfenidone and its Derivatives Induce Vasorelaxation of Small Pulmonary Arteries in Mouse Precision-Cut Lung Slices In Vitro Precision cut lung slices were prepared using a modification of previously reported procedures (see e.g., Jiang et al., 2010, *J. Pharmacol. Exp. Ther.* 334:703-709) and based on the method described by Perez-Joghbi and Sanderson (see e.g., Perez-Joghbi, J. F. and Sanderson, M. J., *Am. J. Physiol.*, 2007, 293:L1000-L1011). Mice were euthanized with $CO_2$, a 2 cm long incision was made in the midline of the neck above the trachea and the trachea was isolated from surrounding tissue. The trachea was cut open and cannulated with PE 90 plastic tubing. A solution of 2% low melting point agarose (Sigma-Aldrich, St. Louis Mo.) in Hanks Buffered Salt solution (HBSS) was prepared at 37° C. Lungs were inflated by injecting 1.2 ml of 2% agarose followed by 0.2 ml of air through the tracheal cannula. The chest was then opened along the midline and the heart was exposed. A solution of 6% gelatin (Sigma-Aldrich, St. Louis Mo.) was prepared in HBSS and 0.4 mL was injected into the right ventricle using a 1 mL syringe and 26 gauge needle, to fill the pulmonary arteries with gelatin. The mouse was cooled to 4° C. for 15 min to harden the agarose and gelatin to stiffen the lung for sectioning. The individual lung lobes were then isolated, glued to a platform and sliced perpendicular to the long axis of the lung. 150 μm thick slices were prepared in ice cold HBSS using an EMS-4000 tissue slicer (Electron Microscopy Sciences, Fort Wash. Pa.). The slices were maintained in sterile, serum-free Dulbecco's modified Eagle's medium (DMEM, Gibco, Grand Island, N.Y.) containing penicillin (100 U/mL, Cellgro, Manassas, Va.), streptomycin (100 μg/mL, Cellgro, Manassas, Va.) and amphotericin B (1.5 μg/mL, Cellgro, Manassas, Va.) at 37° C. and 5% $CO_2$+95% air in a humidified incubator for not more than 3 days.

The method used to measure constriction and relaxation of pulmonary arteries in lung slices is a modification of a method previously described that was used to measure constriction and relaxation of mouse airways (see e.g., Jiang et al., 2010 *J. Pharmacol. Exp. Ther.* 334:703-709). Lung slices were placed on glass coverslips in a 1 mL volume incubation chamber and held in place with nylon mesh (Small Parts Inc, Miami Lakes, Fla.). The chamber was placed on the stage of a Nikon (Melville, N.Y.) TE200 inverted microscope at room temperature and slices incubated in HBSS containing 10 mM HEPES buffer. Pulmonary arteries in lung slices were imaged using a 20× objective and images recorded using a CoolSNAP HQ2 digital camera (Photometrics, Tucson Ariz.). Images in the absence and the presence of the vasoconstrictor 5-HT (Sigma-Aldrich, St. Louis, Mo.) and the vasorelaxants pirfenidone (Sigma-Aldrich, St. Louis Mo.) and CXN-8, CXN-9 and CXN-16 were collected and vasoconstriction and vasorelaxation was calculated by pixel summing of the cross-sectional area of the pulmonary artery lumen before and after addition of the test agent, using ImageJ software (http://imagej.nih.gov). A decrease in cross-sectional area was defined as vasoconstriction while an increase in cross-sectional area was defined as vasorelaxation, as shown in FIGS. 1A-1B.

Relaxation of pulmonary arteries is of special interest for decreasing resistance in pathological situations such as pulmonary hypertension. Experimental evidence supports that both pirfenidone and its derivatives CXN-8, CXN-9 and CXN-16 induced relaxation of small pulmonary arteries in precision-cut lung slices and isolated pulmonary artery rings of mice. The vasoconstrictor serotonin (5-HT, 5-hydroxytryptamine) plays an important role in the pathobiology of pulmonary hypertension (PH).

First, small pulmonary arteries were pre-constricted in mouse precision-cut lung slices with 100 nM 5-HT, a concentration that causes submaximal constriction of pulmonary arteries, as shown in FIG. 1A. Cumulative addition of pirfenidone caused a concentration-dependent relaxation of pre-constricted mouse pulmonary arteries with an $EC_{50}$ of 14.3 μM and maximal relaxation of 81.2±4.8%, as shown in FIG. 1B. The derivatives of pirfenidone CXN-8, CXN-9 and CXN-16 were found to be more potent than pirfenidone. CXN-8 caused a dose-dependent relaxation with an $EC_{50}$ of 5.6 nM and maximal relaxation of 77.1±9.6%. The $EC_{50}$ of CXN-9 and CXN-16 were 69.8 nM and 1.7 respectively (FIG. 1B).

Example 2. Pirfenidone and CXN-8 Induces Vasorelaxation in Mouse Isolated Extralobar Pulmonary Arteries In Vitro Mouse extralobar pulmonary arteries were isolated and prepared using a modification of a previously reported procedure (see e.g., Bockman et al., 1996, *J. Pharmacol. Exp. Ther.* 278:1235-1243). Mice were euthanized with $CO_2$, the chest was opened, and the heart and lung combined were isolated from surrounding tissue. The main pulmonary artery was isolated from its origin at the right ventricle, past its bifurcation into the right and left pulmonary arteries. The artery segment was removed and placed in Krebs solution (composition in mM: NaCl 126, KCl 5.5, $CaCl_2$ 2.5, $NaH_2PO_4$ 1.2, $MgCl_2$ 1.2, $NaHCO_3$ 25, dextrose 11.1, $Na_2Ca$ EDTA 0.029) equilibrated with 95%02-5% $CO_2$ (pH 7.4). The pulmonary artery segment was cleaned of connective tissue and the main pulmonary artery and its right and left branches were cut into 2 mm long rings. The rings were mounted using 2 stainless steel pins (0.1 mm in diameter) passed through the artery lumen. One pin was attached to a Kent isometric force transducer (Kent Scientific Corp, Torrington Conn.) for measurement of isometric tension while the second pin was held in a fixed position. This allowed for measurement of contraction and relaxation of the ring in the circular direction. Mounted rings were placed in 10 mL of Krebs solution in glass muscle chambers (Radnoti, Monrovia, Calif.) gassed with 95% 02-5% $CO_2$, and maintained at 37° C. Rings were washed with Krebs solution and equilibrated for 90-120 min at a passive resting tension of 150 mg before experiments with test agents were started.

Figure 2A:
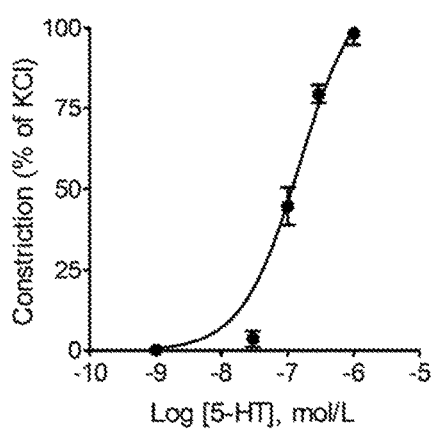
FIGS. 2A-2D show that pirfenidone and its derivative CXN-8 induced relaxation of pre-constricted mouse isolated extralobar pulmonary artery rings.
Figure 2B:
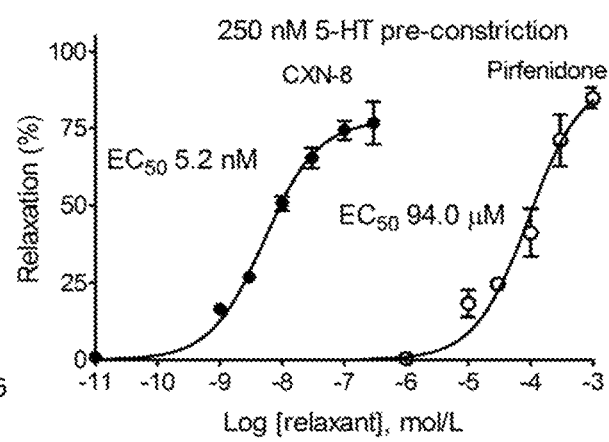
Figure 2C:
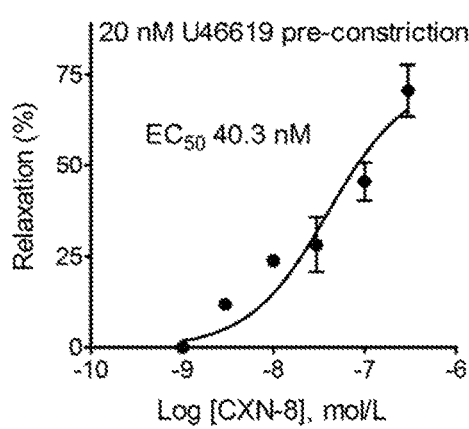
Figure 2D:
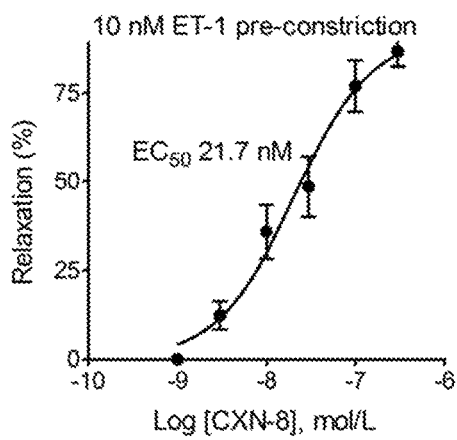

Mouse isolated extralobar pulmonary arteries were pre-constricted with 250 nM 5-HT, a concentration that causes submaximal constriction, as shown in FIG. 2A. Cumulative addition of pirfenidone and CXN-8 caused a concentration-dependent relaxation of mouse pulmonary arteries with a maximal relaxation of 84.9±3.4% and 76.7±7.0%, respectively, as shown in FIG. 2B. CXN-8 was found to be more potent than pirfenidone. The $EC_{50}$ of CXN-8 and pirfenidone are 5.2 nM and 94.0 μM, respectively, as shown in FIG. 2B. Cumulative addition of CXN-8 also caused a concentration-dependent relaxation of mouse pulmonary arteries with a maximal relaxation of 70.6±7.1% in U46619 pre-contracted arteries and 86.6±4.1% in endothelin 1 (ET-1) pre-contracted arteries, respectively. The $EC_{50}$ of CXN-8 in relaxing U46619 and ET-1 pre-contracted arteries was 40.3 nM and 21.7 nM, respectively.

Example 3. CXN-8-Induced Vasorelaxation of Mouse Extralobar Pulmonary Arteries is Both Endothelium-Dependent and Endothelium-Independent The endothelium was removed from pulmonary arteries by inserting a small (200 μm diameter) wire into the inside lumen of the arteries and gently rubbing the internal surface. To test for the presence of functional endothelium, rings with and without rubbing were contracted with 250 nM 5-HT followed by relaxation using 1 µM of the endothelium dependent vasorelaxant acetylcholine. Rings that relaxed by 5% or less were considered as lacking the endothelium. Rings with and without endothelium were used to test the relaxant effects of CXN-8.

The role of the endothelium and nitric oxide in mediating the relaxant effects of CXN-8 was also tested. Endothelial cells are recognized as major regulators of vascular function, and endothelial dysfunction contributes to development of pulmonary hypertension (see e.g., Morrell N W, et al., *J Am Coll Cardiol.* 2009; 54: S20-31; Sakao S et al. *Respir Res.* 2009; 10:95). To investigate the role of endothelium in CXN-8-induced relaxation, the endothelium was removed by rubbing of the intimal surface of isolated pulmonary arteries of mice.

Figures 3A, 3B:
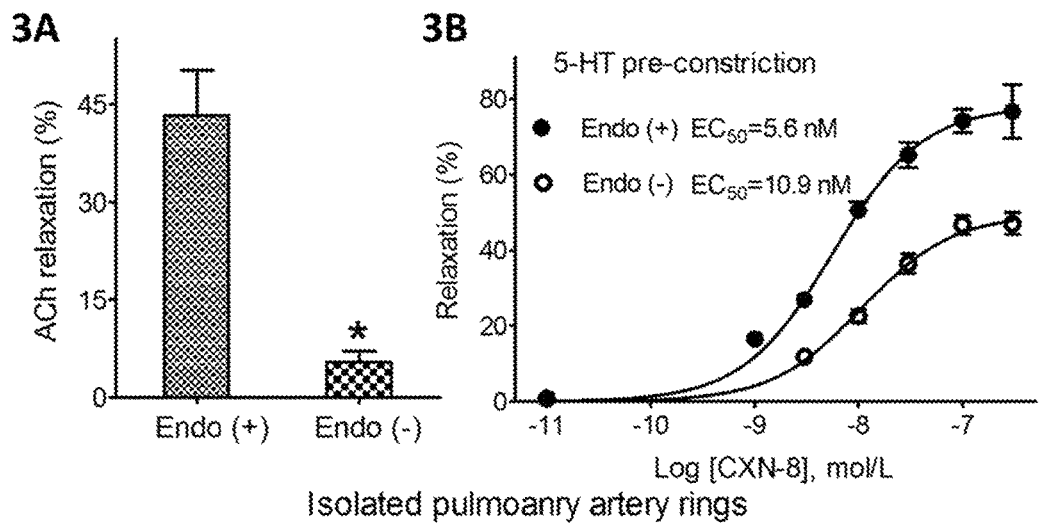
FIGS. 3A-3B show that CXN-8-induced vasorelaxation is both endothelium-dependent and -independent. Isolated mouse pulmonary artery rings with (+) or without (−) endothelium (Endo) were pre-constricted with 250 nM 5-HT followed by treatment with 1 µM Ach to determine the absence or presence of endothelium (FIG. 3A) or different concentrations of CXN-8 (FIG. 3B). Responses (mean±S.E., n=7) represent the % relaxation of the pre-constriction to 5-HT. *p<0.001 vs. with endothelium.

1 µM acetylcholine only induced a 5% relaxation of 250 nM 5-HT-pre-contracted endothelium-denuded mouse pulmonary arteries as compared to 42% relaxation in endothelium-intact arteries, as shown in FIG. 3A. Cumulative addition of CXN-8 still caused a concentration-dependent relaxation of endothelium-denuded arteries, as shown in FIG. 3B. However, endothelium removal significantly reduced the relaxation induced by CXN-8 in pulmonary arteries, which increased the $EC_{50}$ from 5.2 nM to 10.9 nM (p<0.05) and reduced the maximal relaxation from 76.7±7.0% to 47.2±2.9% (p<0.05), as shown in FIG. 3B.

Example 4. CXN-8-Induced Vasorelaxation of Mouse Extralobar Pulmonary Arteries is Both Nitric Oxide (NO)-Dependent and NO-Independent NO is a potent pulmonary arterial vasodilator as well as a direct inhibitor of vascular smooth muscle cell proliferation. The impact of NO has been reflected in its therapeutic role in pulmonary hypertension (PH), as shown by the clinical efficacy of inhaled NO and the NO-dependent phosphodiesterase type-5 inhibitor sildenafil. The use of inhaled NO has been reported in acutely ill patients with severe PH. However, administration of NO over the long term is technically difficult with a significant risk of cytotoxicity.

The synthesis of NO is mediated by a family of NO synthase enzymes. It is well accepted that acetylcholine induces relaxation of pulmonary arteries via endothelium-dependent NO production. Nitric oxide production was inhibited in pulmonary arteries by 30 min incubation with the nitric oxide synthesis inhibitor nitro-L-arginine methyl ester (L-NAME, 100 µM). To test for nitric oxide synthase inhibition by L-NAME, rings were contracted with 250 nM 5-HT followed by relaxation using 1 µM of the nitric oxide dependent vasorelaxant acetylcholine. The relaxant effects of CXN-8 were then tested in rings in the absence (with nitric oxide) and the presence (without nitric oxide) of L-NAME.

Figures 4A, 4B:
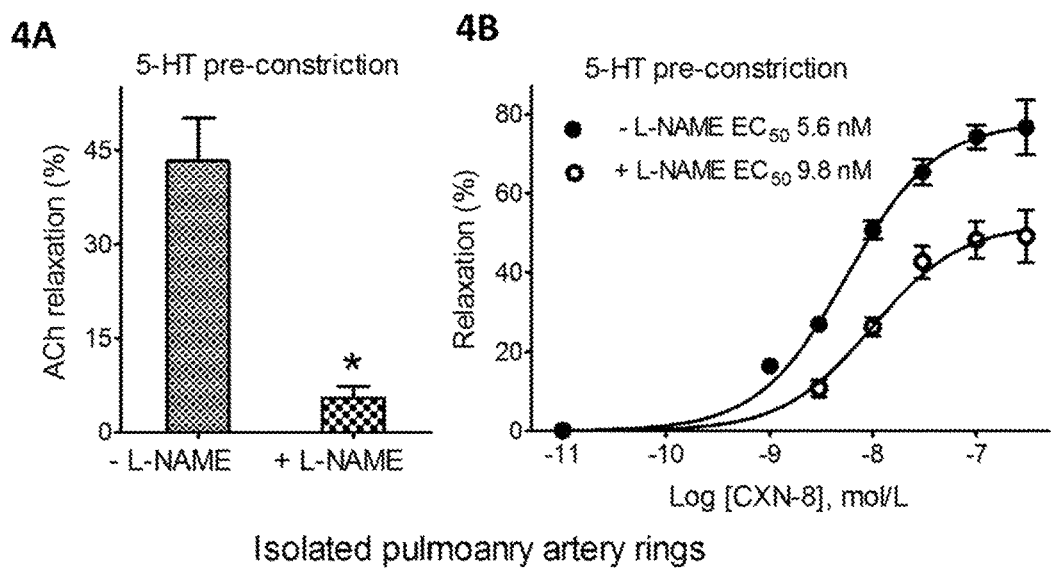
FIGS. 4A-4B show that CXN-8-induced vasorelaxation is both nitric oxide (NO)-dependent and -independent. Isolated pulmonary artery rings were pre-constricted with 250 nM 5-HT in the absence or presence of the nitric oxide synthesis inhibitor nitro-L-arginine methyl ester (L-NAME, 100 µM) followed by treatment with 1 µM ACh (FIG. 4A) or different concentrations of CXN-8 (FIG. 4B). Responses (mean±S.E., n=7) represent the % relaxation of the pre-constriction to 5-HT. *p<0.01 vs. in the absence of L-NAME.

As shown in FIG. 4A, the NOS inhibitor nitro-L-arginine methyl ester (L-NAME, 100 µM) effectively attenuated 1 µM acetylcholine-induced relaxation of 5-HT-pre-contracted mouse pulmonary arteries. Cumulative addition of CXN-8 still caused a concentration-dependent relaxation of arteries in the presence of L-NAME, as shown in FIG. 4B. However, pre-treatment with L-NAME (100 µM) reduced CXN-8-induced relaxation of pulmonary arteries, which increased the $EC_{50}$ from 5.6 nM to 9.9 nM (p<0.05) and reduced the maximal relaxation from 74.5±7.4% to 45.5±6.2% (p<0.05), as shown in FIG. 4B.

Example 5. Efficacy of CXN-8 to Lower Pulmonary Artery Pressure in Mice with Targeted Disruption of the Endothelial NO Synthase Enzyme (eNOS) (Acute Treatment, Intravenous Infusion)

The right ventricular systolic pressure (RVSP) is used to estimate the pressure inside the pulmonary arteries that supply the lung with blood. In general, the RVSP equals the pulmonary artery pressure. Thus, RVSP measurement has become the standard for estimating pulmonary artery pressure. The standard method for obtaining the RVSP and the pulmonary artery pressure is an invasive procedure called a heart catheterization.

Mice (20-25 g) were anesthetized via an intraperitoneal (i.p.) injection of a combination of xylazine (10 mg/kg body weight) and ketamine (100 mg/kg body weight). One-half dose was given as supplemental anesthesia as needed. Animals were placed on a heating pad set to maintain body temperature at approximately 37° C. The neck and upper chest area were cleaned with 70% isopropyl alcohol and a 2 cm long incision was made anterior to the manubrium on the right side and above the jugular fossa. The jugular fossa was identified and the external jugular vein was isolated from surrounding tissue. The anterior projection of the jugular vein was tied off with 8-0 silk suture and a 1 mm incision was made in the jugular vein. A 1 French Mikro-Tip pressure catheter (Millar Inc, Houston, Tex.) catheter was inserted into the jugular vein and advanced through the right atrium into the right ventricle to measure ventricular systolic pressure of mice via a pressure transducer using PowerLab monitoring hardware and software (AD Instruments, Colorado Springs, Colo., USA). The pressure catheter was secured in place using an 8-0 silk suture tied around the catheterized jugular vein. The peak of the right ventricular pressure waveform was taken as the RVSP. A cannula was placed into the right femoral vein for drug dosing.

The left femoral triangle was then cleaned with 70% isopropyl alcohol and a 2 cm long incision was made above the femoral groove. The femoral vein was identified and isolated from the femoral artery and surrounding tissue. The posterior projection of the femoral vein was tied off with 8-0 silk suture and a 1 mm incision was made in the femoral vein. A mouse femoral vein catheter (M-FC STD, Braintree Scientific, Braintree, Mass.) was inserted into the femoral vein and secured in place using an 8-0 silk suture tied around the catheterized femoral vein. The femoral vein catheter was attached to a 0.5 mL syringe for injection of CXN-8 intravenously.

CXN-8 was administered intravenously in a dose-escalation manner in 15 minute intervals from doses of 0.14 mg/kg to 4.6 mg/kg. Hemodynamic indices, including heart rate (HR) and RVSP were measured. At the end of the experiment, mice were euthanized via pentobarbital overdose. A baseline RVSP of >30 mmHg was required to initiate study of the compounds described herein.

NO, synthesized by the eNOS in endothelial cells of the pulmonary vasculature, contributes to the low pressure and resistance which is characteristic of the normal pulmonary circulation. Previous studies have shown an important role of basal NO release in regulating pulmonary vascular tone in both humans and animals (see e.g., Stamler et al., 1994, *Circulation,* 89: 2035-2040; Steudel et al., 1997, *Circ. Res.* 81:34-41). Reduced levels of eNOS have been demonstrated in the pulmonary vasculature of patients with PH, providing a mechanism for dysregulated vasoconstriction in PH. A murine model that genetically lacks eNOS is also more susceptible to developing PH (see e.g., Steudel et al. 1997, *Circ. Res.* 81:34-41; Fagan et al., 1998, *J. Clin. Invest.* 103:291-299).

Figures 5A, 5B, 5C:
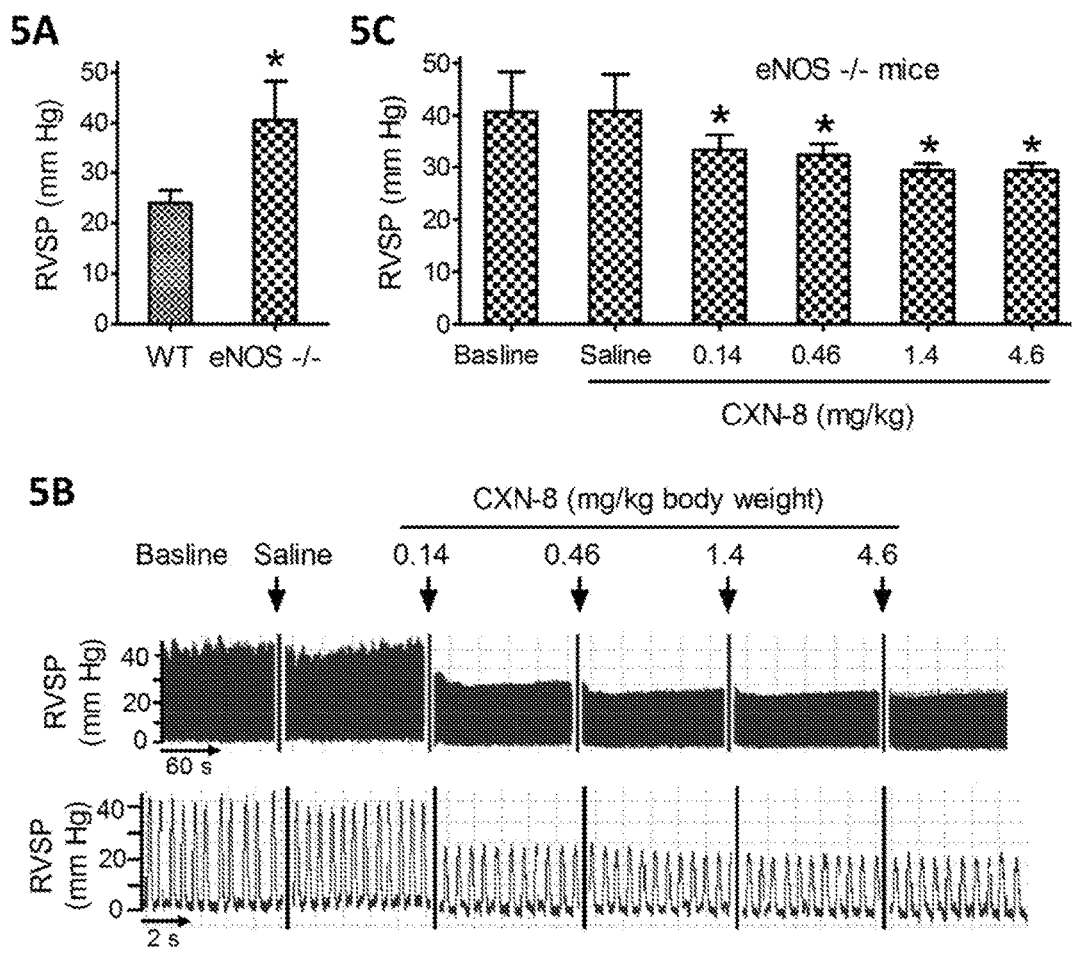
FIGS. 5A-5C show the efficacy of CXN-8 to reduce right ventricular pressure, which is used to measure pulmonary arterial pressure, in eNOS-knockout mice.

As shown in FIG. 5A, eNOS−/− mice have a much higher RVSP as compared to wild-type mice (40.7±7.6 vs. 24.0±2.5 mmHg). Intravenous administration of CXN-8 via the femoral vein significantly lowered RVSP in a dose-dependent manner compared with mice receiving saline, as shown in FIGS. 5B-5C. At a dose of 4.6 mg/kg, the RVSP of mice was reduced from 40.7±7.6 mmHg to 29.3±1.5 mmHg (p<0.05).

Example 6. Efficacy of CXN-8 to Lower Pulmonary Artery Pressure in Mice with Deletion of Regulator of G-Protein Signaling 2 (RGS2) Gene (RGS2−/−) (Acute Treatment, Intravenous Infusion)

Figures 6A, 6B, 6C:
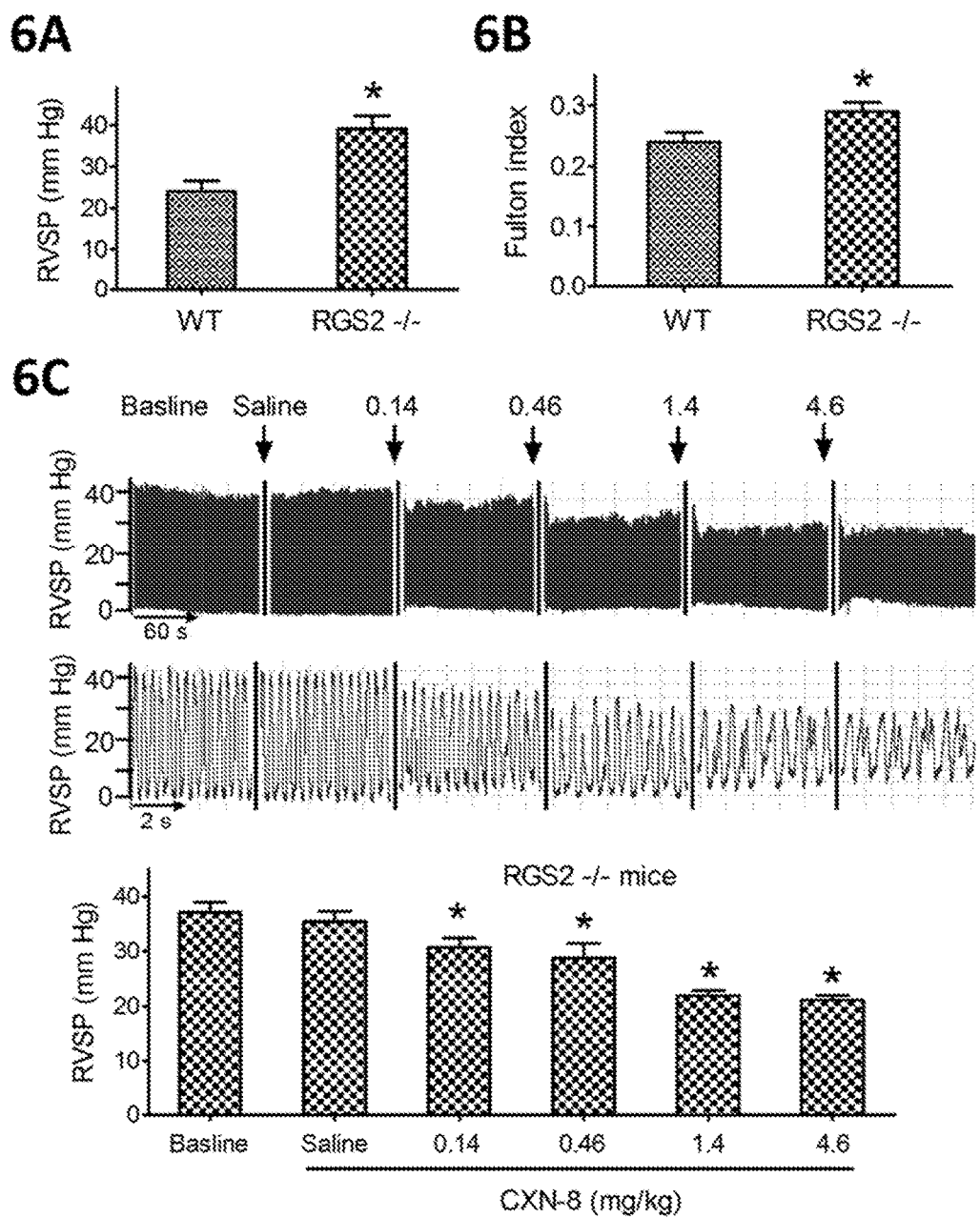
FIGS. 6A-6C show the efficacy of CXN-8 to reduce RVSP in RGS2 knockout mice.

RGS2−/− mice have a significantly higher baseline RVSP (39.0±3.2 mmHg) compared to WT controls (24.0±2.5 mmHg), as shown in FIG. 6A. Loss of RGS2 also caused a 21% increase in the Fulton index, as shown in FIG. 6B, a measure of right ventricular hypertrophy that is also a characteristic feature of pulmonary hypertension. Administration of CXN-8 via the femoral vein resulted in significant lowering of RVSP in a dose-dependent manner compared with mice receiving saline, as shown in FIGS. 6C-6D). At a dose of 4.6 mg/kg, the RVSP of RGS2 KO mice was reduced from 36.7±1.9 mmHg to 19.6±0.9 mmHg.

Example 7. Efficacy of CXN-8 to Lower Pulmonary Artery Pressure in Mice Exposed to Chronic Hypoxia (Acute Treatment, Intravenous Infusion)

Figures 7A, 7B, 7C:
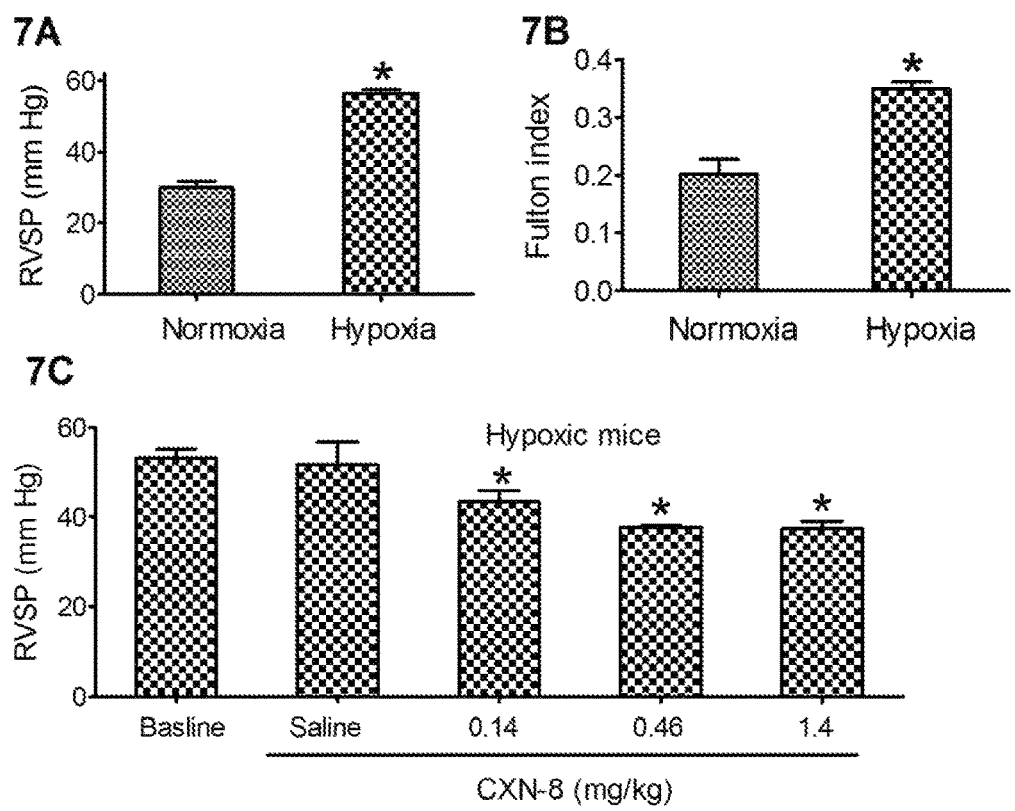
FIG. 7A-7C show the efficacy of CXN-8 to reduce RVSP in a chronic hypoxia model of PH in mice.

Mice maintained in a hypoxic environment, for example at high altitude, develop pulmonary vasoconstriction, medial hypertrophy and increased muscularization of the small arteries (see e.g., Fagan et al, *J. Pharmacol. Exp. Ther.* 2010, 334:703-709). C57BL/6 mice ages 8-10 weeks were housed for three weeks in either ambient conditions or hypobaric hypoxia simulating an altitude of 17,000-foot elevation with a fraction of inspired oxygen ($FIO_2$) of 10%. Chronic expose to hypoxia for three weeks significantly increased RVSP (56.4±1.0 mmHg) compared to normoxic mice (29.0±1.8 mmHg) (FIG. 7A). Chronic expose to hypoxia also caused a 73% increase in the Fulton index (FIG. 7B). Administration of CXN-8 via the femoral vein resulted in significant lowering of RVSP in a dose-dependent manner compared to treatment with saline (FIG. 7C). At a dose of 1.4 mg/kg, the RVSP of hypoxic mice was reduced from 56.4±1.0 mmHg to 37.4±1.7 mmHg.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating pulmonary hypertension in a subject in need thereof, comprising administering to the subject a therapeutically effective amount of a compound of Formula (V):

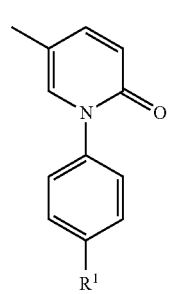

(V)

or a pharmaceutically acceptable salt thereof, wherein:

$R^1$ is —($C_{1-6}$ alkoxy)-($NR^2R^3$); and $R^2$ and $R^3$ are each an independently selected C1-6 alkyl group; or $R^2$ and $R^3$, together with the nitrogen atom to which they are attached, form a monocyclic 4-6 membered heterocycloalkyl ring, wherein the subject does not suffer from idiopathic pulmonary fibrosis.

2. The method of claim 1, wherein the pulmonary hypertension comprises one or more of pulmonary arterial hypertension, pulmonary venous hypertension, hypoxic pulmonary hypertension, thromboembolic pulmonary hypertension, and miscellaneous pulmonary hypertension.

3. The method of claim 1, wherein the pulmonary hypertension comprises pulmonary arterial hypertension.

4. The method of claim 1, further comprising administering to the subject a therapeutically effective amount of a compound selected from the group consisting of a vasodilator, an endothelin receptor antagonist, a calcium channel blocker, an anticoagulant, a diuretic, an anti-bacterial agent, an anti-microbial agent, or an anesthetic.

5. The method of claim 4, wherein the vasodilator is selected from the group consisting of nitric oxide, acetylcholine, prostacyclin, epoprostenol, and sildenafil.

6. The method of claim 1, further comprising administering to the subject supplemental oxygen therapy.

7. The method of claim 1, wherein the administration is oral administration.

8. The method of claim 1, wherein the administration is pulmonary administration.

9. The method of claim 1, wherein $R^2$ and $R^3$ are each an independently selected $C_{1-3}$ alkyl.

10. The method of claim 1, wherein $R^1$ is —$OCH_2CH_2CH_2CH_2N(CH_3)_2$.

11. The method of claim 1, wherein $R^1$ is —($C_{1-6}$ alkoxy)-(4-6 membered heterocycloalkyl).

12. The method of claim 1, wherein $R^1$ is —$OCH_2CH_2CH_2$-(4-6 membered heterocycloalkyl) or —$OCH_2CH_2CH_2CH_2$-(4-6 membered heterocycloalkyl).

13. The method of claim 1, wherein $R^1$ is selected from the group consisting of

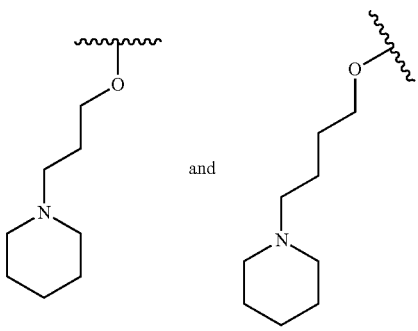
14. The method of claim 1, wherein the compound is selected from the group consisting of:
   5-methyl-1-(4-(3-(piperidin-1-yl)propoxy)phenyl)pyridin-2(1H)-one;
   5-methyl-1-(4-(4-(piperidin-1-yl)butoxy)phenyl)pyridin-2(1H)-one; and
   1-(4-(4-(dimethylamino)butoxy)phenyl)-5-methylpyridin-2(1H)-one;
   or a pharmaceutically acceptable salt thereof.
* * * * *

UNITED STATES PATENT AND TRADEMARK OFFICE
CERTIFICATE OF CORRECTION

PATENT NO. : 10,420,759 B2
APPLICATION NO. : 15/482014
DATED : September 24, 2019
INVENTOR(S) : Tu et al.

Page 1 of 1

It is certified that error appears in the above-identified patent and that said Letters Patent is hereby corrected as shown below:

In the Claims

Column 24, Line 17, Claim 1, delete "C1-6" and insert -- $C_{1-6}$ --

Column 24, Line 24, Claim 4, delete "or" and insert -- and --

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*